United States Patent
Furuuchi et al.

(10) Patent No.: US 9,687,147 B2
(45) Date of Patent: Jun. 27, 2017

(54) OPTICAL COHERENCE TOMOGRAPHY DEVICE AND CONTROL PROGRAM

(71) Applicant: NIDEK CO., LTD., Gamagori-shi, Aichi (JP)

(72) Inventors: Yasuhiro Furuuchi, Gamagori (JP); Masaaki Hanebuchi, Gamagori (JP); Masakazu Endo, Gamagori (JP); Hajime Namiki, Gamagori (JP); Naoki Takeno, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 14/955,579

(22) Filed: Dec. 1, 2015

(65) Prior Publication Data
US 2016/0150954 A1    Jun. 2, 2016

(30) Foreign Application Priority Data

Dec. 2, 2014    (JP) .................................. 2014-243585
Dec. 2, 2014    (JP) .................................. 2014-243586

(51) Int. Cl.
*A61B 3/14*    (2006.01)
*A61B 3/00*    (2006.01)
(Continued)

(52) U.S. Cl.
CPC ............ *A61B 3/102* (2013.01); *A61B 3/0025* (2013.01); *A61B 3/1005* (2013.01); *G01B 9/02045* (2013.01); *G01B 9/02091* (2013.01)

(58) Field of Classification Search
USPC ............................................... 351/200–246
See application file for complete search history.

(56) References Cited

U.S. PATENT DOCUMENTS

| | | | |
|---|---|---|---|
| 2012/0120408 A1 | 5/2012 | Yasuno et al. | |
| 2013/0176532 A1* | 7/2013 | Sharma | A61B 3/102 351/206 |
| 2015/0374228 A1* | 12/2015 | Satake | G06T 7/0016 351/206 |

FOREIGN PATENT DOCUMENTS

WO    2010/143601 A1    12/2010

OTHER PUBLICATIONS

Hendargo et al., "Automated Non-Rigid Registration and Mosaicing for Robust Imaging of Distinct Retinal Capillary Beds Using Speckle Variance Optical Coherence Tomography," Biomedical Optics Express, May 2013, vol. 4, No. 6, pp. 803-821.
(Continued)

*Primary Examiner* — Mohammed Hasan
(74) *Attorney, Agent, or Firm* — Oliff PLC

(57) ABSTRACT

An optical coherence tomography device includes an OCT optical system; a processor. The processor executes: an image generation processing of processing first OCT signals, and generating, based on the first OCT signals, a three-dimensional motion contrast image which is obtained by imaging a moving object in the scanning position; a Doppler shift detection processing of detecting Doppler shift in a scanning position specified on the three-dimensional motion contrast image, the plurality of second OCT signals being detected at timings different from the timings when the plurality of first OCT signals are detected; and a velocity obtaining processing of obtaining an absolute velocity of the moving object based on the Doppler shift detected by the Doppler shift detection processing and a three-dimensional structure of the test subject obtained from the three-dimensional motion contrast image generated by the image generation processing.

20 Claims, 10 Drawing Sheets

(51) Int. Cl.
    A61B 3/10      (2006.01)
    G01B 9/02     (2006.01)

(56)         References Cited

OTHER PUBLICATIONS

Zhao et al., "Phase-Resolved Optical Coherence Tomography and Optical Doppler Tomography for Imaging Blood Flow in Human Skin with Fast Scanning Speed and High Velocity Sensitivity," Optics Letters, Jan. 2000, vol. 25, No. 2, pp. 114-116.
Mariampillai et al., "Speckle Variance Detection of Microvasculature Using Swept-Source Optical Coherence Tomography," Optics Letters, Jul. 2008, vol. 33, No. 13, pp. 1530-1532.
Srinivasan et al., "Rapid Volumetric Angiography of Cortical Microvasculature with Optical Coherence Tomography," Optics Letters, Jan. 2010, vol. 35, No. 1, pp. 43-45.
Trasischker et al., "In Vitro and in vivo Three-Dimensional Velocity Vector Measurement by Three-Beam Spectral-Domain Doppler Optical Coherence Tomography," Journal of Biomedical Optics, Nov. 2013, vol. 18, No. 11, pp. 116010-1 thru 116010-11.

* cited by examiner

OPTICAL COHERENCE TOMOGRAPHY DEVICE AND CONTROL PROGRAM

CROSS REFERENCE TO RELATED APPLICATIONS

This application is based upon and claims the benefit of priorities of Japanese Patent Application No. 2014-243585 filed on Dec. 2, 2014 and Japanese Patent Application No. 2014-243586 filed on Dec. 2, 2014, the contents of which are incorporated herein by reference in its entirety.

BACKGROUND ART

The present invention relates to an optical coherence tomography device obtaining motion contrast data of a test subject and to a control program.

As one of the optical coherence tomography devices (also referred to as OCT devices) of the prior art, for example, a device measuring retinal blood flow is known. This device exploits a fact that the frequency of measurement light radiated to a subject's eye changes due to the Doppler effect of blood cells or the like flowing in blood vessels.

RELATED ART DOCUMENT

Patent Document 1: International Publication No. 2010/143601
Non-Patent Document 1: H. C. Hendargo et al. Biomed. Opt. Express, Vol. 4, No. 6, p. 803/May 2013
Non-Patent Document 2: Yonghua Zhao et al. OPTICS LETTERS/Vol. 25, No. 2/Jan. 15, 2000
Non-Patent Document 3: Adrian Mariampillai et al. OPTICS LETTERS/Vol. 33, No. 13/Jul. 1, 2008
Non-Patent Document 4: Vivek J. Srinivasan et al. OPTICS LETTERS/Vol. 35, No. 1/Jan. 1, 2010
Non-Patent Document 5: "In vitro and in vivo three-dimensional velocity vector measurement by three-beam spectral-domain Doppler optical coherence tomography", Wolfgang Trasischker, J. Biomed. Opt. 18(11), 2013

SUMMARY

In recent years, an OCT device has been suggested which obtains images of the blood flow of micro-sized blood vessels by using an OCT technique without using a contrast agent. However, it is difficult to easily measure an absolute blood flow velocity by using OCT devices of the prior art.

The present invention has been made to solve the above problem, and a technical object thereof is to provide an optical coherence tomography device, which can easily obtain an absolute blood flow velocity of a test subject, and a non-transitory computer readable recording medium storing a control program.

In order to achieve the above object, the present invention has the following configurations.

An optical coherence tomography device comprising:
an OCT optical system including a scanner configured to scan a test subject by measurement light, the OCT optical system being configured to detect an OCT signal generated based on the measurement light and reference light corresponding to the measurement light;
a processor; and
memory storing instructions, when executed by the processor, causing the optical coherence tomography device to execute:
an image generation processing of processing a plurality of first OCT signals, which are temporally different from each other with respect to a same position on the test subject, and generating, based on the plurality of first OCT signals, a three-dimensional motion contrast image, which is obtained by imaging distribution of a moving object in a depth direction in each of the scanning position;
a Doppler shift detection processing of processing a plurality of second OCT signals which are temporally different from each other with respect to the same position on the test subject, and detecting Doppler shift in a depth direction in a scanning position specified on the three-dimensional motion contrast image, the plurality of second OCT signals being detected at timings different from the timings when the plurality of first OCT signals are detected; and
a velocity obtaining processing of obtaining an absolute velocity of the moving object based on the Doppler shift detected by the Doppler shift detection processing and a three-dimensional structure of the test subject obtained from the three-dimensional motion contrast image generated by the image generation processing.

A non-transitory computer readable medium storing a control program used in an optical coherence tomography device including an OCT optical system including a scanner configured to scan a test subject by measurement light, the OCT optical system being configured to detect an OCT signal generated based on the measurement light and reference light corresponding to the measurement light, the control program, when executed by a processor of the optical coherence tomography device, causing the optical coherence tomography device to execute:
an image generation processing of processing a plurality of first OCT signals, which are temporally different from each other with respect to a same position on the test subject, and generating, based on the plurality of first OCT signals, a three-dimensional motion contrast image, which is obtained by imaging distribution of a moving object in a depth direction in each of the scanning position;
a Doppler shift detection processing of processing a plurality of second OCT signals which are temporally different from each other with respect to the same position on the test subject, and detecting Doppler shift in a depth direction in a scanning position specified on the three-dimensional motion contrast image, the plurality of second OCT signals being detected at timings different from the timings when the plurality of first OCT signals are detected; and
a velocity obtaining processing of obtaining an absolute velocity of the moving object based on the Doppler shift detected by the Doppler shift detection processing and a three-dimensional structure of the test subject obtained from the three-dimensional motion contrast image generated by the image generation processing.

An optical coherence tomography device comprising:
an OCT optical system including a scanner configured to scan a test subject by measurement light, the OCT optical system being configured to detect an OCT signal generated based on the measurement light and reference light corresponding to the measurement light;
a processor; and
memory storing instructions, when executed by the processor, causing the optical coherence tomography device to execute:
a motion contrast obtaining processing of obtaining motion contrast of a plurality of OCT signals obtained at a first time interval with respect to the same position on the test subject and obtaining a profile of a phase difference between the plurality of OCT signals, wherein when the profile of the phase difference is discontinuous, the motion contrast obtaining process obtains the motion contrast of the plurality of OCT signals at a second time interval different from the first interval.

An optical coherence tomography device comprising:

an OCT optical system including a scanner configured to scan a test subject by measurement light, the OCT optical system being configured to detect an OCT signal generated based on the measurement light and reference light corresponding to the measurement light;

a processor; and memory storing instructions, when executed by the processor, causing the optical coherence tomography device to execute:

a motion contrast obtaining processing of obtaining motion contrast of a plurality of OCT signals which is obtained at a first time interval with respect to a same position on the test subject, and obtaining a profile of a phase difference between the plurality of OCT signals;

a three-dimensional structure obtaining processing of obtaining a three-dimensional structure of a blood vessel of the test subject based on the motion contrast; and a blood vessel information obtaining processing of obtaining at least either a diameter or a type of a blood vessel based on the three-dimensional structure of the blood vessel, wherein when the profile of the phase difference between the plurality of OCT signals is discontinuous, the motion contrast obtaining processing obtains the motion contrast of the plurality of OCT signals obtained at a second time interval different from the first time interval based on the diameter or the type of the blood vessel obtained by the blood vessel information obtaining processing, the second time interval being preset according to the obtained diameter or the type of the blood vessel.

A non-transitory computer readable medium storing a control program used in an optical coherence tomography device including an OCT optical system including a scanner configured to scan a test subject by measurement light, the OCT optical system being configured to detect an OCT signal generated based on the measurement light and reference light corresponding to the measurement light, the control program, when executed by a processor of the optical coherence tomography device, causing the optical coherence tomography device to execute:

obtaining a phase difference of a plurality of OCT signals, which is obtained at a first time interval with respect to a same position on the test subject; and obtaining a phase difference of a plurality of OCT signals which is obtained at a second time interval different from the first time interval when a profile of the obtained phase difference is discontinuous.

DESCRIPTION OF ILLUSTRATIVE EMBODIMENTS

Figure 1:
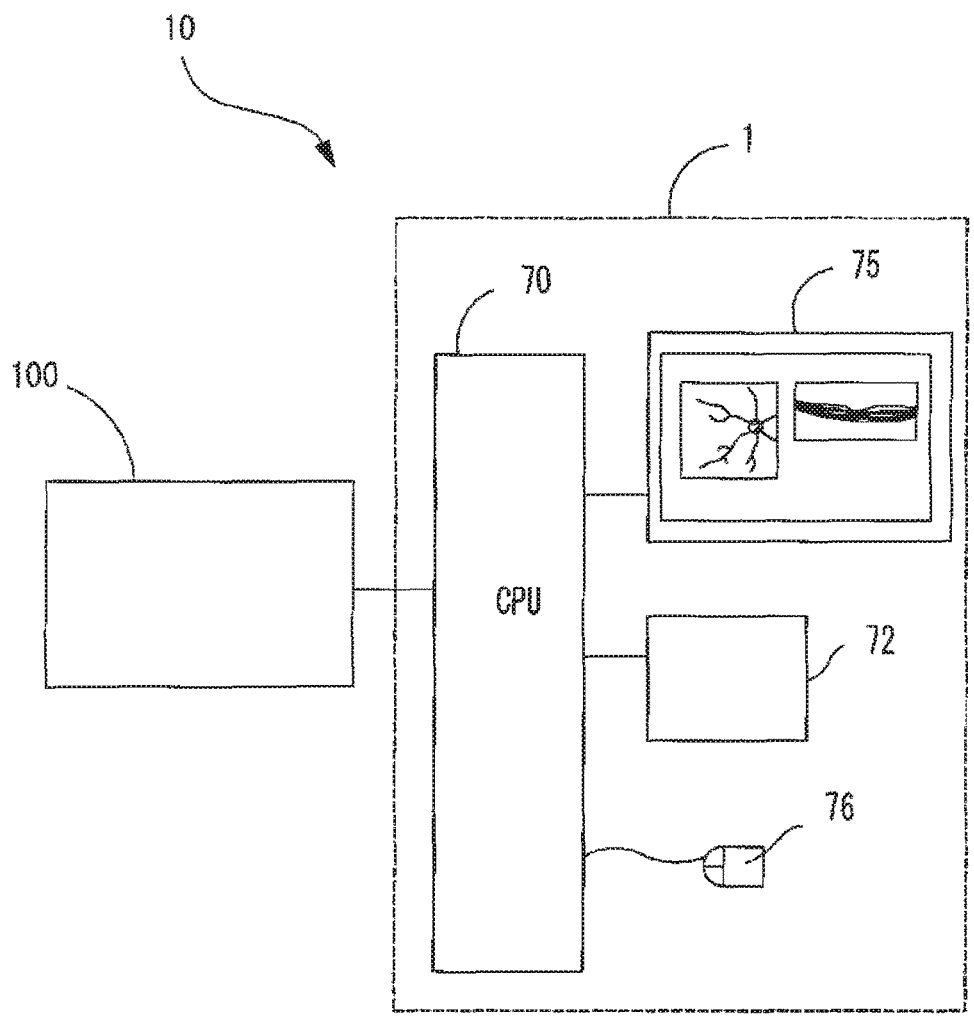
FIG. 1 is a block diagram illustrating the constitution of an optical coherence tomography device.

Hereinafter, a first embodiment according to the present invention will be described based on FIGS. 1 to 10. An optical coherence tomography device (such as an optical coherence tomography device 10) of the first embodiment obtains a motion contrast image of a test subject. The motion contrast is detection information such as the motion of a test subject and the temporal change. For example, a flow image or the like is a kind of the motion contrast image. For example, the flow image is obtained by detecting the motion of fluid or the like and making the motion into an image. A contrast angiogram or the like, in which the position of blood vessels obtained by detecting the motion of blood are shown by contrast, can be mentioned as a kind of the motion contrast image.

For instance, the optical coherence tomography device of the first embodiment (hereinafter, simply referred to as a "present device" in some cases) mainly includes an OCT optical system (such as an OCT optical system 100, an image generation portion (such as a control portion 70), a Doppler shift detection portion (such as a control portion 70), and a velocity obtainment portion (such as the control portion 70).

For example, the OCT optical system detects an OCT signal generated from measurement light scanning a test subject by a scanner (such as an optical scanner 108) and reference light corresponding to the measurement light. For example, the image generation portion processes a plurality of OCT signals which is temporally different from each other with respect to a same position on the test subject. Furthermore, for example, the image generation portion generates a three-dimensional motion contrast image, which is obtained by forming the distribution of a moving object in a depth direction of each scanning position into an image, based on the plurality of OCT signals. The Doppler shift detection portion processes a plurality of OCT signals, which is detected at a time different from the time the plurality of OCT signals for generating the three-dimensional motion contrast image is detected and temporally different from each other with respect to the same position on the test subject. In addition, for example, the Doppler shift detection portion detects Doppler shift in a depth direction in a scanning position specified on the three-dimensional motion contrast image. For example, the velocity obtainment portion obtains an absolute velocity of the moving object, based on the Doppler shift detected by the Doppler shift detection portion and a three-dimensional structure of the test subject obtained from the three-dimensional motion contrast image generated by the image generation portion. In this way, the present device can measure the absolute velocity of the moving object based on the three-dimensional motion contrast image and the Doppler shift. The present device can also easily measure, for example, an absolute blood flow velocity in the test subject.

The present device may further include an observation optical system (such as an en-face observation optical system 200), an association portion (such as the control portion 70), a deviation detection portion (such as the control portion 70), and a scanning position correction portion (such as the control portion 70). For example, the observational optical system obtains an observation image of the test subject. For example, the association portion associates a scanning position specified on the three-dimensional motion contrast image with the observation image obtained by the observation optical system. For example, the deviation detection portion detects the positional deviation between the observation image associated with the scanning position and the current observation image obtained by the observation optical system by image processing. For example, the scanning position correction portion corrects the scanning position of the measurement light used at the time of detecting the Doppler shift by controlling the driving of the scanner based on the detection result of the positional deviation detected by the deviation detection portion. In this way, even when the position deviation of the test subject occurs, the absolute velocity of the moving object can be excellently measured.

The specific device position is a specific scanning position which is a scanning position specified on the three-dimensional motion contrast image.

The present device may further include a signal receiver (such as the control portion 70) and a first scanning position setting portion (such as the control portion 70). For example, the signal receiver receives an operation signal output from an operation portion (such as an operation portion 76) by an operation of an examiner. For example, the first scanning position setting portion sets the position specified on the three-dimensional motion contrast image based on the operation signal received by the signal receiver as a scanning position of the measurement light used at the time of detecting the Doppler shift.

The velocity obtainment portion may obtain an absolute blood flow velocity, based on the Doppler shift detected by the Doppler shift detection portion and a three-dimensional structure of the test subject's blood vessels obtained from the three-dimensional motion contrast image generated by the image generation portion.

The present device may further include a second scanning position setting portion (such as the control portion 70). For example, the second scanning position setting portion obtains a movement direction of the moving object based on the three-dimensional structure of the test subject and sets a scanning position in a direction orthogonal to the obtained movement direction as a scanning direction.

For example, when the moving object is blood flowing in a blood vessel, the movement direction of the moving object corresponds to the axis direction of a blood vessel designated by the examiner or the like. For example, the same is true for the case where the moving object is lymph flowing in a lymphatic vessel. The movement direction may be three-dimensionally obtained. In the case of a blood vessel, the direction orthogonal to the blood vessel corresponds to, for example, the radial direction of the designated blood vessel.

The present device may be provided with either or both of the first and second scanning position setting portions and may selectively use the first and second scanning position setting portions.

The present device may further include a scan width setting portion (such as the control portion 70). For example, when the three-dimensional structure of the test subject is a three-dimensional structure of a blood vessel, the scan width setting portion may obtain the size of the blood vessel diameter based on the three-dimensional structure of the blood vessel. Furthermore, the scan width setting portion may set the scan width of the measurement light to be greater than the obtained size of the blood vessel diameter. In this way, for example, the examiner can easily check the distribution of the blood flow in the blood vessel.

The present device may further include a time interval control portion (such as the control portion 70). For example, when the three-dimensional structure of the test subject is the three-dimensional structure of a blood vessel, the time interval control portion may obtain the blood vessel diameter based on the three-dimensional structure of the blood vessel. Furthermore, for example, according to the obtained size of the blood vessel diameter, the time interval control portion may change the time interval of irradiation performed in the same position. In this way, for example, non-lapped signals having a high signal-to-noise ratio can be obtained.

For example, the observation optical system may be either an infrared imaging optical system which images a test subject by using infrared light or a scanning laser ophthalmic optical system which images a test subject by using a confocal optical system.

The present device may further include a first control portion (such as the control portion 70). For example, by controlling the scanner such that the measurement light scans plural times each of a plurality of scan lines, the first control portion may obtain a plurality of OCT signals as a basis of the three-dimensional motion contrast image for each of the scan lines.

The present device may further include a second control portion (such as the control portion 70). For example, by controlling the scanner such that the measurement scans plural times the scan line corresponding to scanning position specified on the three-dimensional motion contrast image, the second control portion may obtain a plurality of OCT signals as a basis of Doppler shift.

<First Control Portion>

In the case where a plurality of OCT signals as a basis of the three-dimensional motion contrast image is obtained for each of the scan lines, the following method can be considered. Herein, each of the plurality of scan lines is formed in different positions with respect to a sub-scanning direction. For example, a rectangular scanning area may be formed of the plurality of scan lines. In this case, the control portion controls the scanner such that the measurement light scans the rectangle (raster scanning).

In this case, the control portion may cause the measurement light to scan once each of the plurality of scan lines and then cause the measurement light to scan again the same position. Furthermore, the control portion may perform scanning plural times for each of the scan lines and then perform in other scan lines. In addition, after performing scanning plural times for each of the scan lines, the control portion may perform scanning in other scan lines so as to finish a round of scanning for the respective lines and then perform scanning again with respect to the same position.

<Second Control Portion>

For example, the scanning position designated on the three-dimensional motion contrast image may be set according to a certain scanning pattern (such as linear scanning, circular scanning, or crisscross scanning). In this case, a scanning pattern is used in which the scanning area of the measurement light is narrow compared to the case of the scanning for obtaining the three-dimensional motion contrast image.

For example, the present device may include a processor (such as the control portion 70) and execute a program for measuring velocity stored in a memory or the like. The program for measuring velocity includes, for example, an image generation step, a Doppler shift detection step, and a velocity obtainment step. For example, the image generation step is a step of processing a plurality of OCT signals, which is temporally different from each other with respect to the same position on the test subject, and generating a three-dimensional motion contrast image, which is obtained by forming the distribution of a moving object in a depth direction in each scanning position into an image, based on the plurality of OCT signals. For example, the Doppler shift detection step is a step of processing a plurality of OCT signals, which is detected at a time different from the time the plurality of OCT signals for generating the three-dimensional motion contrast image is detected and temporally different from each other with respect to the same position on the test subject, and detecting Doppler shift in a depth direction in a scanning position specified on the three-dimensional motion contrast image. For example, the velocity obtainment step is a step of obtaining an absolute velocity of the moving object, based on the Doppler shift detected in the Doppler shift detection step and a three-dimensional structure of the test subject obtained from the three-dimensional motion contrast image generated in the image generation step.

Hereinafter, a second embodiment of the present invention will be described based on FIGS. 1 to 11F. For example, the optical coherence tomography device of the second embodiment mainly includes an OCT optical system (such as an OCT optical system 200) and an obtainment portion (such as the control portion 70). For example, the OCT optical system may obtain an OCT signal (coherent signal) generated from measurement light scanning a test subject by a scanner (such as the optical scanner 108) and reference light corresponding to the measurement light. For example, the obtainment portion obtains motion contrast of a plurality of OCT signals obtained at a first time interval with respect to the same position on the test subject. When a profile of a phase difference between the plurality of OCT signals as a basis of the motion contrast, is discontinuous, the obtainment portion may obtain motion contrast of a plurality of OCT signals obtained at a second time interval different from the first time interval. The obtainment portion may change the time interval so as to prevent the profile of the phase difference from becoming discontinuous. Herein, the second time interval may be shorter than the first time interval. In this way, by obtaining the motion contrast having a continuous profile, the examiner can easily check the distribution or the like of the moving object or the like.

The present device may further include a determination portion (such as the control portion 70). For example, the determination portion may detect a slope of the profile of the phase difference obtained by the obtainment portion and determine whether or not the profile of phase difference is continuous based on the detected slope.

The present device may further include a driving control portion (such as the control portion 70). For example, when the profile of the phase difference is discontinuous, the driving control portion may change the time interval of irradiation with respect to the same position by controlling the driving of the scanner. For instance, the driving control portion may shorten the time interval of irradiation with respect to the same position.

When the obtained profile of the phase difference is discontinuous, the obtainment portion may select at least one group of OCT signals obtained at the second time interval different from the first time interval, from the plurality of OCT signals obtained at the first time interval. Furthermore, the obtainment portion may obtain motion contrast of the selected group of OCT signals selected.

For example, the obtainment portion may select every other signal among the plurality of OCT signals obtained at the first time interval and obtain motion contrast based on the selected OCT signals. In this way, for example, the obtainment portion obtains obtained motion contrast based on the plurality of OCT signals obtained at the second time interval two times greater than the first time interval. Likewise, the obtainment portion may alternately select the signals such as every third signal, every fourth signals, or the like. In this way, even if the driving of the scanner is not intentionally controlled, a calculative time interval T can be changed.

For example, when the profile of the phase difference between the plurality of OCT signals as a basis of the motion contrast is continuous, the obtainment portion may obtain motion contrast of the plurality of OCT signals obtained at the second time interval longer than the first time interval so as to increase a signal-to-noise ratio of the motion contrast.

The present device may further include a blood vessel information obtainment portion (such as the control portion 70). For example, the blood vessel information obtainment portion obtains at least either a diameter or a type of a blood vessel based on a three-dimensional structure of the test subject's blood vessel. When the profile of the phase difference between the plurality of OCT signals as a basis of motion contrast is discontinuous, based on the diameter or the type of the blood vessel obtained by the blood vessel information obtainment portion, the obtainment portion may obtain motion contrast of the plurality of OCT signals obtained at the second time interval different from the first time interval preset according to the obtained diameter or type of the blood vessel.

For example, the present device may include a processor (such as the control portion 70) or the like so as to execute a control program stored in a memory or the like. For example, the control program includes an obtainment step. For instance, the obtainment step is a step of obtaining motion contrast of a plurality of OCT signals obtained at the first time interval with respect to the same position on the test subject, and obtaining a phase difference of a plurality of OCT signals obtained at the second time interval different from the first time interval when the obtained profile of the phase difference is discontinuous.

<Example>

Hereinafter, one of the typical examples of the present invention will be described with reference to drawings. FIG. 1 is a block diagram illustrating the constitution of an optical coherence tomography device 10 according to the present example (hereinafter, referred to as a "present device" in some cases). For example, the present device 10 will be described as a fundus imaging device obtaining a tomogram of fundus of a subject's eye.

An OCT control system 1 processes detection signals obtained by the OCT optical system 100. The OCT control system 1 has the control portion 70. For example, the OCT optical system 100 captures a tomogram of fundus Ef of a subject's eye E. For example, the OCT optical system 100 is connected to the control portion 70.

Figure 2:
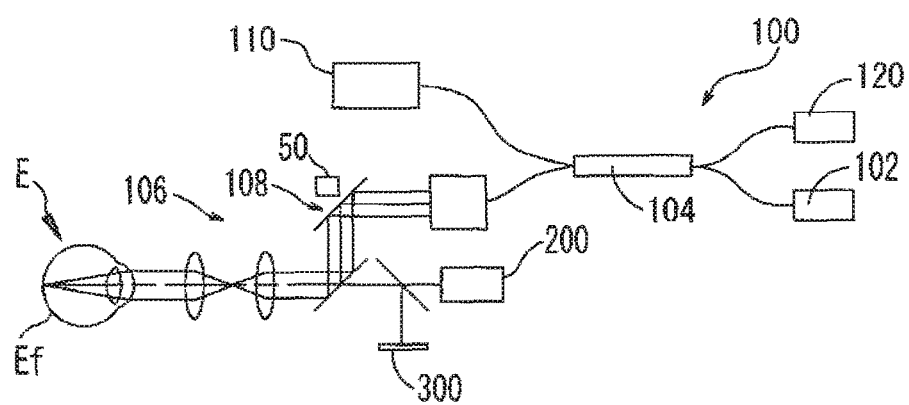
FIG. 2 is a view schematically showing an optical system.

The OCT optical system 100 will be described based on FIG. 2. The OCT optical system 100 irradiates fundus with measurement light. The OCT optical system 100 detects the state of coherence between the measurement light reflected from the fundus and reference light by using a light receiving element (a detector 120). In order to change the imaging position on the fundus Ef, the OCT optical system 100 includes an irradiation position changing unit (such as the optical scanner 108 or a fixation target projection unit 300) changing the irradiation position of the measurement light on the fundus Ef. The control portion 70 controls the operation of the irradiation position changing unit based on the preset imaging position information and obtains a tomogram based on the light receiving signal from the detector 120.

<OCT Optical System>

The OCT optical system 100 has a device constitution of a so-called optical coherence tomography (OCT) and captures a tomogram of an eye E. By using a coupler (a light splitter) 104, the OCT optical system 100 splits light emitted from a light source 102 into the measurement light (sample light) and the reference light. By using a measurement optical system 106, the OCT optical system 100 guides the measurement light to the fundus Ef of the eye E and the reference light to a reference optical system 110. The OCT optical system 100 causes the detector (light receiving element) 120 to receive coherent light synthesized from the measurement light reflected from the fundus Ef and the reference light.

The detector 120 detects an OCT signal generated from the measurement light and the reference light. In a case of Fourier domain OCT, the spectral intensity of the coherent light (spectral OCT signal) is detected by the detector 120, and the OCT signal is obtained by Fourier transform performed on the spectral intensity data. For example, by calculating an absolute value of amplitude in a plurality of OCT signals, a profile (A-scan signal) in a depth direction (A-scanning direction) in a predetermined range is obtained. By lining up luminance profiles in the depth direction in each of the scanning positions of the measurement light used for scanning by the optical scanner 108, an OCT image data (tomographic data) is obtained. Herein, the luminance profile in the OCT image data is a sequence of numbers obtained by lining up luminance values of each pixel in a depth direction in an A-Scan line, and is a graph of depth direction versus luminance value.

The three-dimensional OCT data may be obtained by causing the measurement light to perform two-dimensional scanning. Furthermore, from the three-dimensional OCT data, an en-face OCT image (such as an integrated image obtained by integrating images regarding the depth direction) may be obtained.

A functional OCT signal may be obtained by processing OCT signals. By lining up the functional OCT signals (motion contrast data) in each of the scanning positions of the measurement light used for scanning by the optical scanner 108, functional OCT image data (motion contrast image data) is obtained. Furthermore, three-dimensional functional OCT image data (three-dimensional motion contrast data) may be obtained by causing the measurement light to perform two-dimensional scanning. In addition, from the three-dimensional functional OCT image date, a functional en-face OCT image (such as an en-face Doppler image or an en-face speckle variance image) may be obtained.

Examples of the OCT optical system 100 include spectral-domain OCT (SD-OCT) and swept-source OCT (SS-OCT). The OCT optical system 100 may also be time-domain OCT (TD-OCT).

In the case of SD-OCT, a low-coherent light source (broadband light source) is used as the light source 102, and the detector 120 is provided with a spectral optical system (spectrometer) that splits coherent light into the respective frequency components (respective wavelengths components). The spectrometer is composed of, for example, a diffraction grating and a line sensor.

In the case of SS-OCT, as the light source 102, a wavelength scanning light source which temporally changes an emission wavelength at a high speed (tunable light source) is used, and a single light receiving element is provided as the detector 120, for example. The light source 102 is constituted with, for example, a light source, a fiber ring resonator, and a wavelength-selective filter. Examples of the wavelength-selective filter include a combination of a diffraction grating and a polygon mirror and those using Fabry Perot etalon.

By the coupler 104, the light emitted from the light source 102 is split into a measurement light beam and a reference light beam. The measurement light beam passes through optical fiber and then is emitted to the air. Through other optical members of the optical scanner 108 and the measurement optical system 106, the light beam is condensed on the fundus Ef. Then the light reflected from the fundus Ef returns to the optical fiber through the same optical path.

The optical scanner 108 causes the measurement light to two-dimensionally (XY direction (horizontal direction)) scan the fundus. The optical scanner 108 is disposed in a position approximately conjugate to pupil. The optical scanner 108 is, for example, composed of two galvano mirrors whose reflection angle is arbitrarily adjusted by a driving mechanism 50.

In the manner described above, the reflection (progress) direction of the light beam emitted from the light source 102 is changed, and the light beam scans the fundus Ef in an arbitrary direction. As a result, the imaging position on the fundus Ef is changed. The optical scanner 108 may have any constitution as long as it deflects light. For example, in addition to a reflecting mirror (a galvano mirror, a polygon mirror, or a resonant scanner), an acousto-optical modulator (AOM) changing the progress (deflection) direction of light, and the like are used.

The reference optical system 110 generates the reference light which is synthesized with the reflected light obtained by the reflection of the measurement light from the fundus Ef. The reference optical system 110 may be a Michelson type or a Mach-zenhder type. The reference optical system 110 is formed of, for example, a reflection optical system (such as a reference mirror). By being reflected from the reflection optical system, the light from the coupler 104 returns to the coupler 104 and is guided to the detector 120. For another example, the reference optical system 110 is formed of a transmission optical system (such as optical fiber), and guides the light from the coupler 104 to the detector 120 by transmitting it without causing the light to return to the coupler 104.

The reference optical system 110 has a constitution which changes a difference in an optical path length between the measurement light and the reference light by moving optical members in the path of the reference light. For example, a reference mirror is moved in the optical axis direction. The constitution for changing the difference in the optical path length may be disposed in the path of the measurement light of the measurement optical system 106.

<En-Face Observation Optical System>

The en-face observation optical system 200 is provided to obtain an en-face observation image of the fundus Ef. The en-face observation optical system 200 includes, for example, an optical scanner that two-dimensionally scans the fundus by using the measurement light (such as infrared light) emitted from the light source, and a second light receiving element that receives the reflected light from the fundus through a confocal aperture disposed in a position approximately conjugate to the fundus. The en-face observation optical system 200 has a device constitution of a so-called scanning laser ophthalmoscopy (SLO). For example, while the OCT optical system 100 is obtaining the OCT signals, the en-face observation optical system 200 may continually obtain an en-face observation image.

The en-face observation optical system 200 may have a constitution of a so-called fundus camera. Furthermore, the OCT optical system 100 may also function as the en-face observation optical system 200. That is, the en-face observation image may be obtained by using the data forming a two-dimensionally obtained tomogram (such as an integrated image in a depth direction of a three-dimensional tomogram, an integration value of spectral data in each of X and Y positions, luminance data in each of X and Y positions in a certain depth direction, or an image of a superficial layer of retina).

<Fixation Target Projection Unit>

The fixation target projection unit 300 has an optical system for leading the direction of a line of vision of the eye E. The ftxation target projection unit 300 has a fixation target presented to the eye E and can lead the eye E to a plurality of directions.

For Example, the fixation target projection unit 300 has a visible light source emitting visible light and two-dimensionally changes the position where the target is presented. In this way, the direction of the line of vision is changed, and as a result, the imaging site is changed. For example, when the fixation target is presented in the same direction as the imaging optical axis, the central portion of the fundus is set as the imaging site. Furthermore, when the fixation target is presented above the imaging optical axis, the upper portion of the fundus is set as the imaging site. That is, according to the position of the target relative to the imaging optical axis, the imaging site is changed.

For example, as the fixation target projection unit 300, various constitutions are considered such as a constitution in which the fixation position is adjusted according to a lighting position of LED arranged in the form of matrix and a constitution in which light from the light source is used for scanning by the optical scanner and the fixation position is adjusted by controlling the lighting of the light source. Furthermore, the fixation target projection unit 300 may be an internal fixation lamp type or an external fixation lamp type.

<Control Portion>

The control portion 70 includes CPU (processor), RAM, ROM, and the like. The CPU of the control portion 70 controls the entire device (the OCT control system 1 and the OCT optical system 100) including the members having the respective constitutions. The RAM temporarily stores various pieces of information. The ROM of the control portion 70 stores various programs for controlling the operation of the entire device, initial values, and the like. The control portion 70 may be constituted with a plurality of control portions (that is, a plurality of processors).

As shown in FIG. 1, the control portion 70 is electrically connected to a nonvolatile memory (storage portion) 72, an operation portion (control portion) 76, a display portion (monitor) 75, and the like. The nonvolatile memory (memory) 72 is a non-temporary storage medium which can retain the stored contents even when power supply is shut off. For example, as the nonvolatile memory 72, it is possible to use a hard disk drive, a flash ROM, a detachable USB memory, and the like. The memory 72 stores an imaging control program for controlling capturing of an en-face image and a tomogram performed by the OCT optical system 100. Furthermore, the memory 72 stores a signal processing program which can process the OCT signals obtained by the OCT control system 1. The memory 72 also stores various pieces of information on imaging, such as a tomogram (OCT data) in a scan line, a three-dimensional tomogram (three-dimensional OCT data), an en-face fundus image, and the information on the imaging position of the tomogram. The examiner inputs various operation instructions into the operation portion 76.

The operation portion 76 outputs signals to the control portion 70 in response to the input operation instructions. In the operation portion 76, for example, at least any of a mouse, a joystick, a keyboard, a touch panel, and the like may be used.

The display portion 75 may be either a display mounted on the body of the device or a display connected to the body. A display of a personal computer (hereinafter, referred to as "PC") may also be used, and a plurality of displays may be concurrently used. Furthermore, the display portion 75 may be a touch panel. When the display portion 75 is a touch panel, the display portion 75 functions as an operation portion. On the display portion 75, various images including the tomograms and en-face images captured by the OCT optical system 100 are displayed.

<Capturing of Motion Contrast Image>

Figure 3:
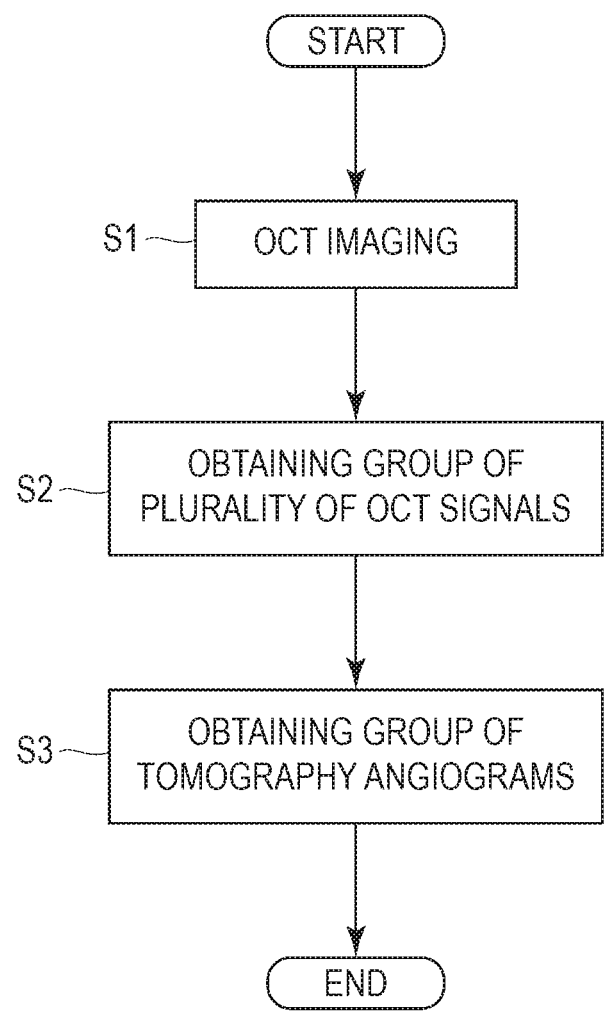
FIG. 3 is a flowchart for illustrating processing of examples of the present invention.

Hereinafter, by using FIG. 3, the methods for operating and controlling the present device 10 at the time of capturing a motion contrast image will be described. For example, the control portion 70 includes a processor (such as CPU) performing various control processing and a storage medium storing a program. According to the program, the processor executes the following processing. In the following description, each step will be denoted by a number for differentiation, but the order of the denoting numbers does not necessarily agree with the actual control order.

First, an examiner instructs a test subject to stare at a fixation target of the fixation target projection unit 300. Thereafter, while watching an observation image of an anterior eye segment, which is captured by a camera for observing an anterior eye segment not shown in the drawing, through the display portion 75, the examiner performs an alignment operation by using the operation portion 76 (such as a joystick not shown in the drawing) such that a measurement optical axis is positioned at the center of the pupil of the subject's eye.

(Step 1: OCT Imaging)

Figure 4:
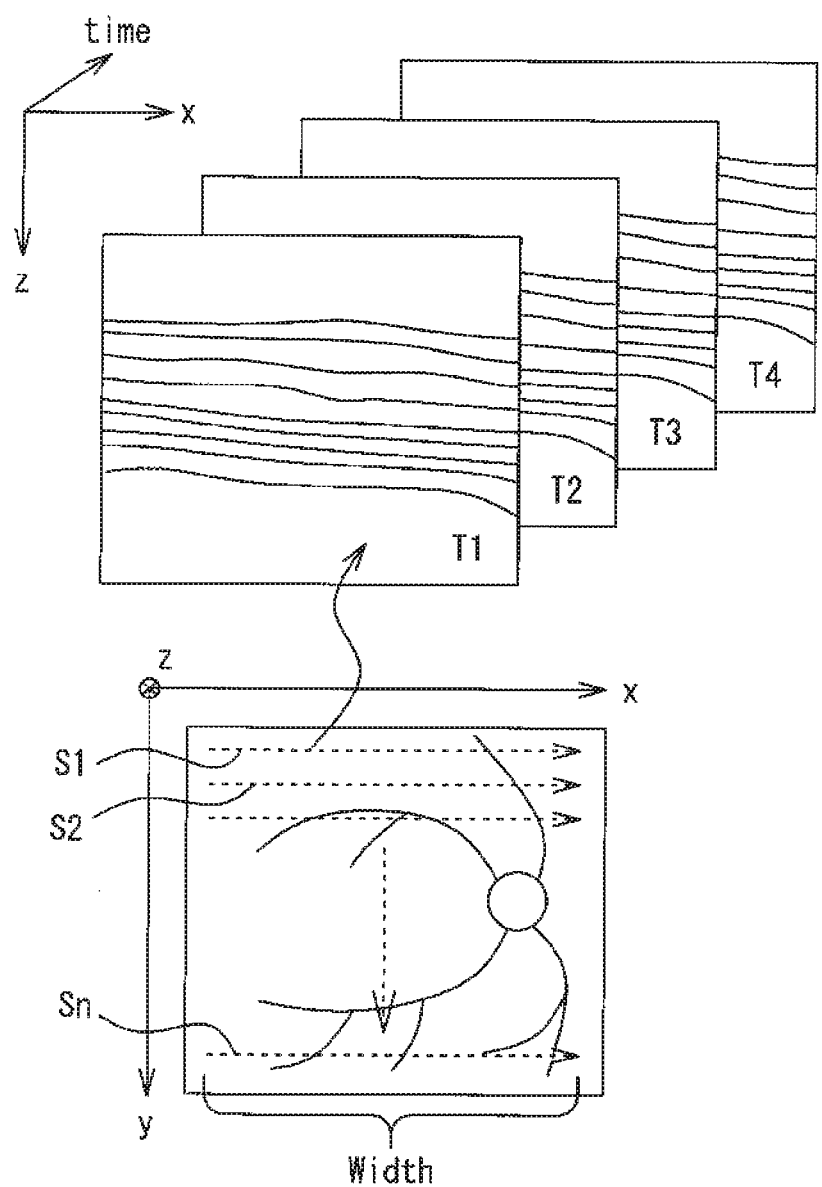
FIG. 4 shows a fundus image for illustrating the measurement of examples of the present invention.

In the same position, the control portion 70 obtains at least two frames of OCT signals that are temporally different from each other. For example, the control portion 70 controls the driving of the optical scanner 108 such that the optical scanner scans the fundus by using the measurement light. For example, the optical scanner 108 is caused to perform scanning along a first scan line S1 shown in FIG. 4 in an x direction. Herein, the scanning in the horizontal direction (such as the x direction) performed by the measurement light is called "B scanning". In the following description, a single frame of OCT signal means an OCT signal obtained by the B scanning performed once. The control portion 70 obtains an OCT signal detected by the detector 120 during scanning. In FIG. 4, the z-axis direction is the direction of the optical axis of the measurement light; the x-axis direction is a direction which is a horizontal direction perpendicular to the z-axis; and the y-axis direction is a direction which is a vertical direction perpendicular to the z-axis.

When a first scanning is completed, the control portion 70 performs a second scanning in the same position as the first scanning. For example, the control portion 70 performs scanning along the scan line S1 shown in FIG. 4 by using the measurement light and then again performs scanning along the scan line S1 by using the measurement light. The control portion 70 obtains an OCT signal detected by the detector 120 during the second scanning. In this way, the control portion 70 can obtain two frames of OCT signals which are temporally different from each other with respect to the same position. In the present example, scanning is repeated four times in the same position, thereby obtaining four continuous frames of temporally different OCT signals. For example, the control portion 70 repeats the scanning in the scan line S four times, thereby obtaining four frames of OCT signals. Here, the number of the frames is not limited to four, and at least two or more frames of temporally different OCT signals may be obtained.

When temporally different signals can be obtained from the same position through a single scanning, the second scanning may not be performed. For example, in a case where two measurement lights whose optical axes deviate from each other at a predetermined interval are simultaneously used for scanning, scanning does not need to be performed plural times. What matters is that the OCT signals, which are temporally different from each other with respect to the same position, need to be able to be obtained.

The control portion 70 also obtains at least two frames of temporally different signals in other positions. As shown in FIG. 4, in the first scan line S1, for example, y=y1. Furthermore, in the second scan line S2, for example, y=y2. After obtaining temporally different signals in the first scan line S1, the control portion 70 subsequently obtains at least two frames of temporally different OCT signals in the second scan line S2.

As shown in FIG. 4, the control portion 70 performs raster scanning by using the measurement light and obtains at least two or more frames of temporally different OCT signals in each of the scan lines. In this way, three-dimensional information on the inside of the fundus can be obtained.

The raster scanning has a scanning pattern in which the measurement light scans the fundus in the form of a rectangle. The raster scanning is used for, for example, scanning an en-face image.

(Step 2: Obtaining a Group of a Plurality of OCT Signals)

Thereafter, by processing the OCT signals obtained by the OCT optical system 100, the control portion 70 obtains a plurality of OCT signals. For example, the control portion 70 performs Fourier transform on the OCT signals (coherent signals) obtained in Step 1. Herein, a signal in a position of (x,y) of the n-th sheet in an N frame is represented by An (x,z). Through the Fourier transform, the control portion 70 obtains a plurality of OCT signals represented by An (x,z). The plurality of OCT signals represented by An (x,z) includes a real number component and an imaginary number component.

(Step 3: Obtaining a Group of Tomography Angiograms)

Then, by processing the plurality of OCT signals obtained by Step 2, the control portion 70 obtains a group of tomography angiograms (a group of motion contrast images). As the method for processing the plurality of OCT signals, for example, it is possible to consider a method of calculating a phase difference between the plurality of OCT signals, a method of calculating a vector difference between the plurality of OCT signals, a method of multiplying the phase difference by the vector difference of the plurality of OCT signals, and the like. In the present example, the method of calculating a phase difference will be described.

First, the control portion 70 calculates a phase difference between the plurality of OCT signals represented by A(x,z) that are obtained at two or more different times at least in the same position. For instance, by using Equation (1), the control portion 70 calculates the change of the phase. In the present example, for example, measurement is performed at four different times at least. Therefore, the calculation is performed three times in total regarding T1 and T2, T2 and T3, and T3 and T4, and three data are calculated. In the equation, An represents a signals obtained at a time Tn, and * represents a complex conjugate.

$$\Delta\Phi_n(x,z)=\arg(A_{n+1}(x,z)\times A_n^*(x,z)) \quad (1)$$

For example, the control portion 70 may remove noise by calculating the average of the three frames of signals. Because the nose components randomly exist in each frame, the noise components are reduced compared to the signal components by calculating the average.

Figure 5:
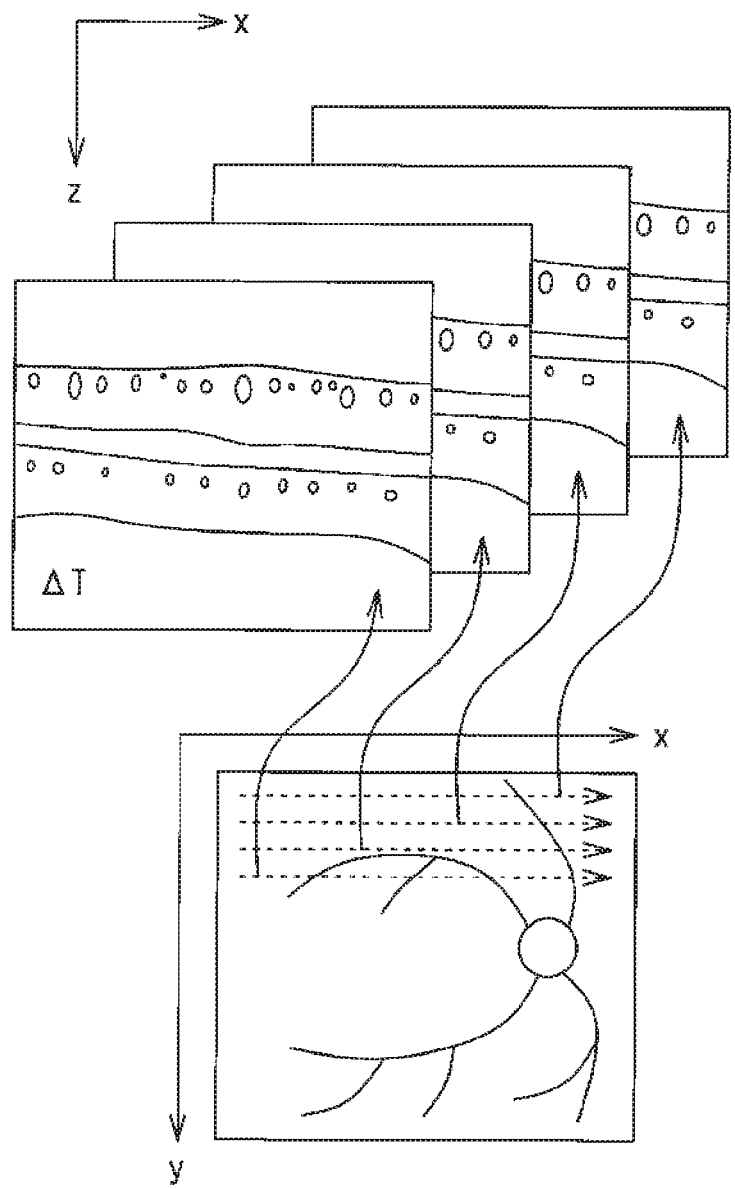
FIG. 5 shows a tomography angiogram.

As described so far, the control portion 70 obtains the profile in the depth direction relating to the phase difference between the plurality of OCT signals and creates gradation according to the size of the profile, thereby obtaining a functional OCT image of the test subject. By repeating the aforementioned processing for each of the scan lines, the control portion 70 generates tomography angiograms for each of the scan lines as shown in FIG. 5. In this way, the control portion 70 obtains a three-dimensional motion contrast image.

<Measurement of Blood Flow>

Figure 6:
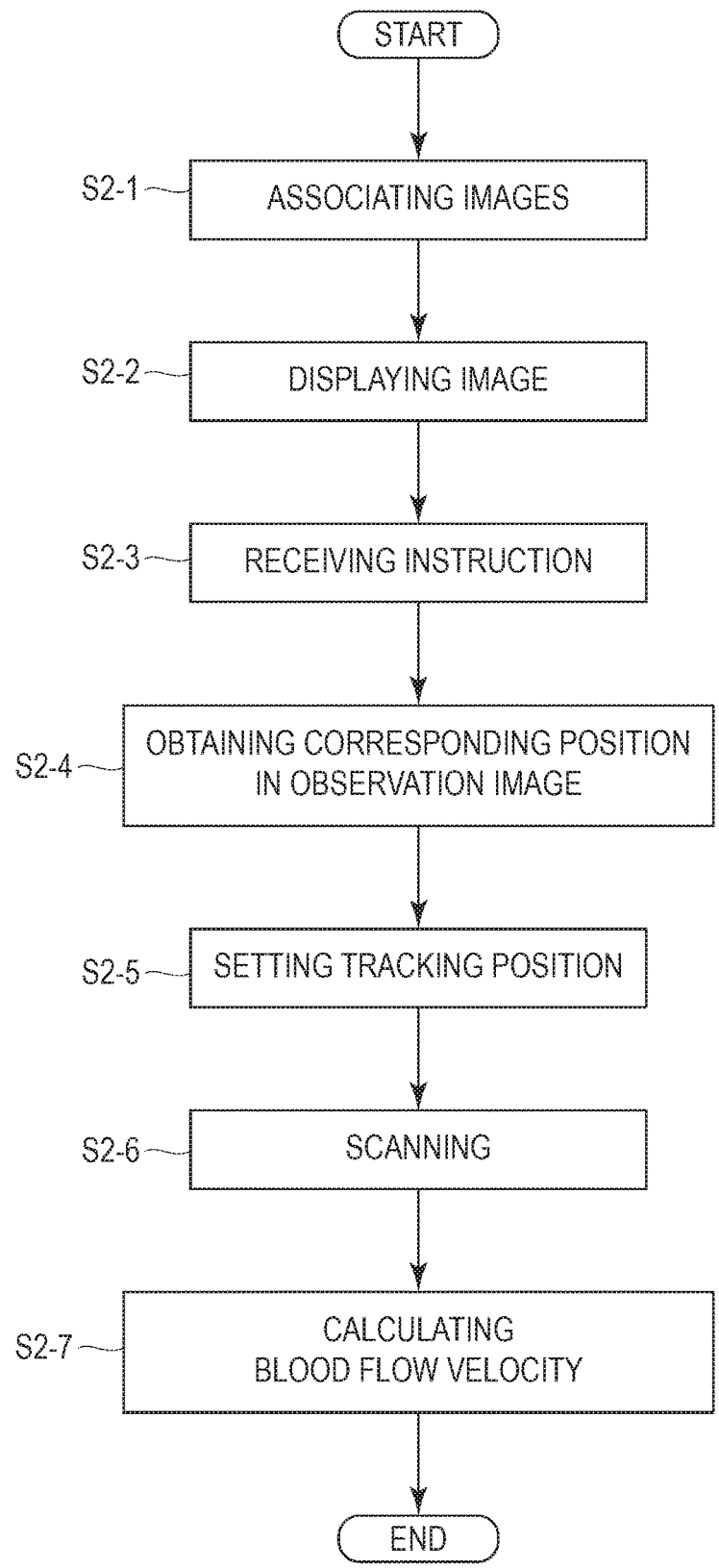
FIG. 6 is a flowchart illustrating the control of blood flow measurement of examples of the present invention.

Based on FIG. 6, a method for determining a blood flow velocity by using the motion contrast image captured in the aforementioned manner will be described. In the present example, by using a three-dimensional structure of a blood vessel obtained from the three-dimensional motion contrast image, an absolute blood flow velocity is determined. For determining the absolute blood flow velocity, first, the control portion 70 associates the motion contrast image with the observation image (such as an SLO image or an infrared image of fundus) captured by the en-face observation optical system 200 (Step 2-1). The observation image associated with the motion contrast image may be either an observation image, which is captured at the time of obtaining the OCT signals by the OCT optical system 100), or an observation image captured after the motion contrast image is generated.

Figure 7:
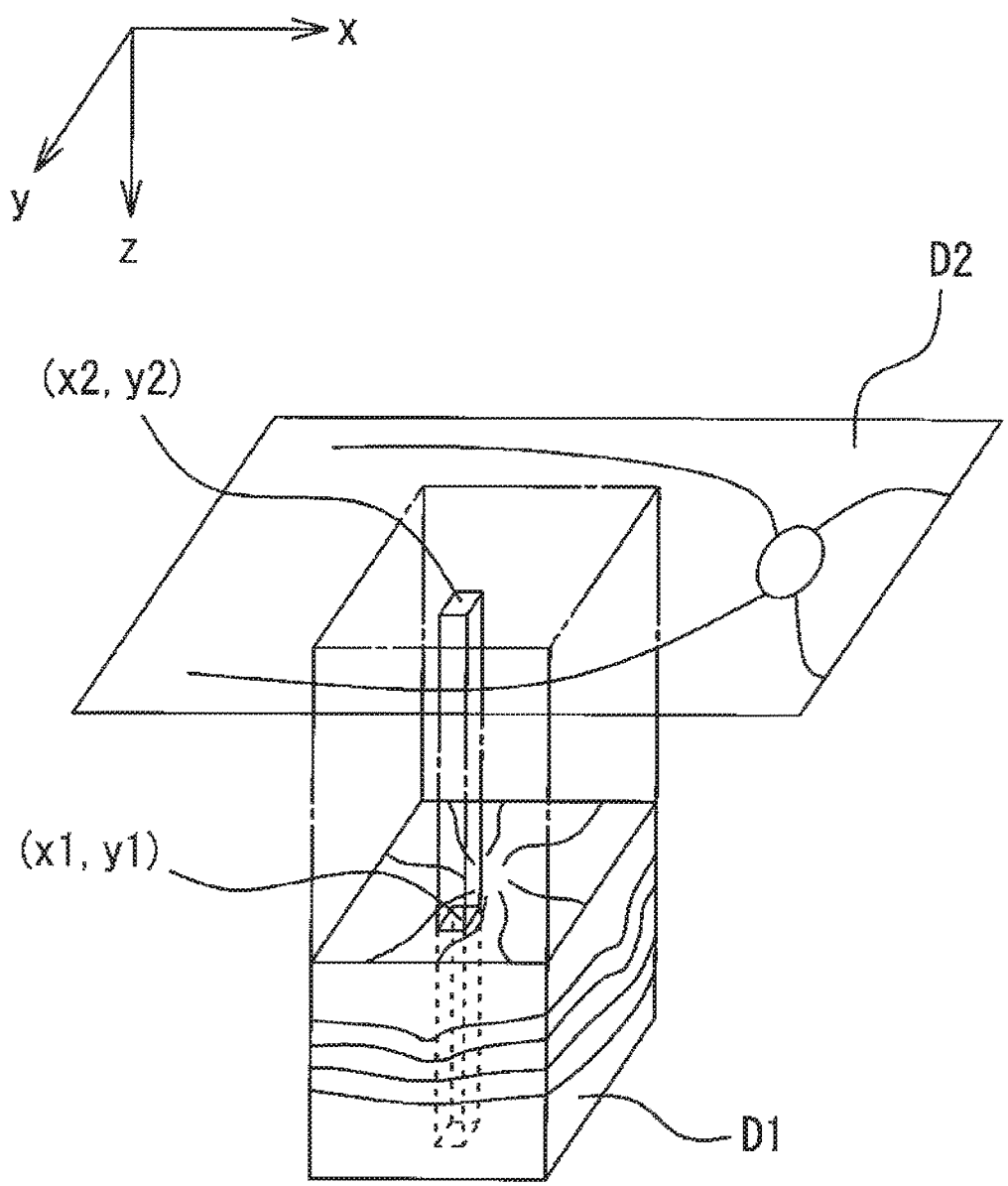
FIG. 7 is a view illustrating the way a motion contrast image and an observation image are associated with each other.

As shown in FIG. 7, for example, the control portion 70 associates coordinates in the XY direction in a two-dimensional observation image D2 with coordinates in the XY direction in a three-dimensional motion contrast image D1. Examples of the association method include a method of using a lighting position of a fixation lamp, a method of using the position of a blood vessel, and the like. When the lighting position of the fixation lamp is used, for example, based on the relationship between the lighting position of the fixation lamp at the time when the motion contrast image D1 is obtained and the lighting position of the fixation lamp at the time when the observation image D2 is obtained, the motion contrast image D1 and the observation image D2 may be associated with each other. When the position of a blood vessel is used, for example, the position of a blood vessel shown in the observation image D2 and the position of a blood vessel shown in the motion contrast image D1 may be detected respectively by image processing, and the motion contrast image D1 and the observation image D2 may be associated with each other such that the positions of the blood vessels agree with each other.

The control portion 70 may associates, for example, the position of a pixel of the motion contrast image D1 with the position of a pixel of the observation image D2. For instance, if the coordinates of a certain pixel of the motion contrast image D1 are (x1,y1), the coordinates (x2,y2) of a pixel of the observation image D2 corresponding thereto may be associated with the coordinates (x1,y1).

In this way, the control portion 70 may associate the observation image D2 with the motion contrast image D1 in advance and use the thus obtained association information for determining the absolute blood flow velocity. The control portion 70 may store the association information in the memory 72.

Figure 8:
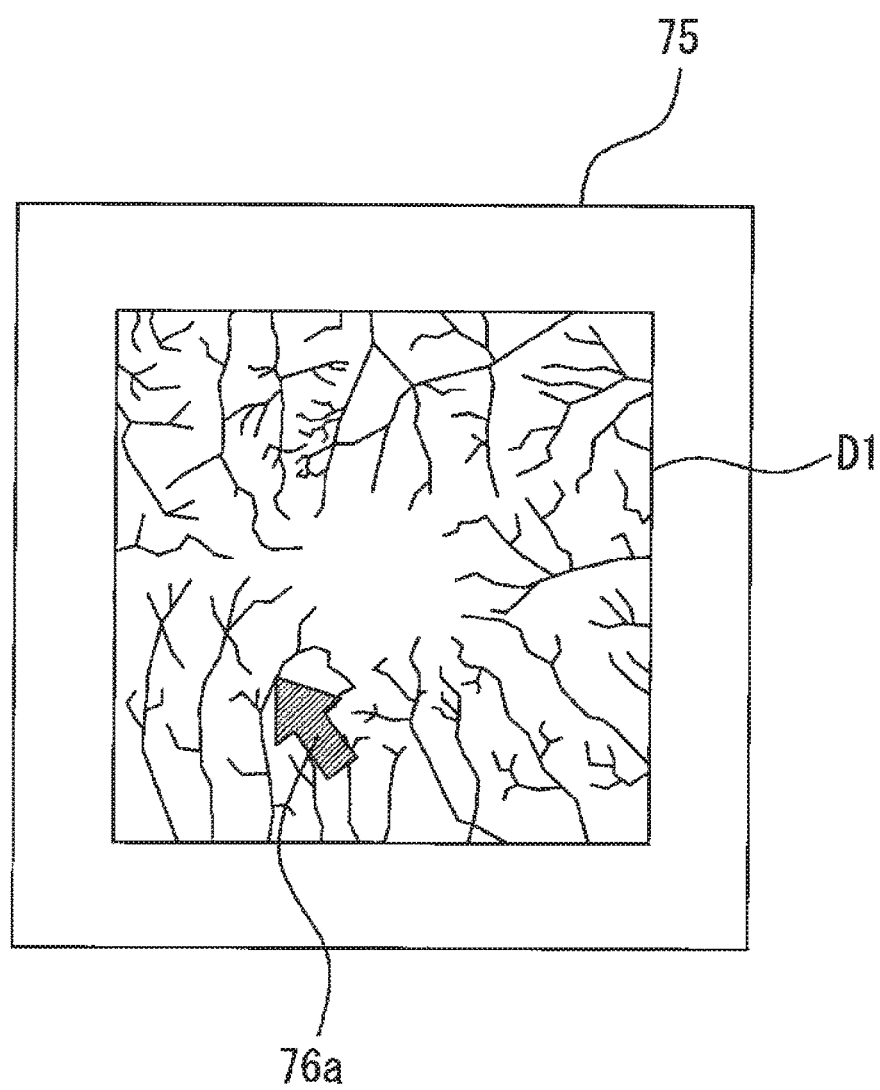
FIG. 8 is a view showing an example of a motion contrast image displayed on a display portion.

Subsequently, as shown in FIG. 8, the control portion 70 displays the motion contrast image D1 obtained as above on the screen of the display portion 75 (Step 2-2). For example, the motion contrast image D1 displayed on the display portion 75 may be a three-dimensional image or a two-dimensional image. In the examples shown in FIG. 8, a two-dimensional image which is obtained by performing addition processing on three-dimensional data in a certain depth area is displayed. In this case, the depth area subjected to the addition processing may be arbitrarily set.

The examiner checks the motion contrast image D1 and designates a blood vessel whose blood flow will be measured. For example, by clicking or touching a pointing device (such as a mouse or a touch panel) of the operation portion 76, the examiner may input the position of the motion contrast image D1 and designate a blood vessel. In the example shown in FIG. 8, the control portion 70 displays a pointer 76a which can move in response to the operation of the operation portion 76. For instance, the examiner moves the pointer 76a displayed on the screen onto a blood vessel of interest and performs an operation such as clicking, thereby designating a blood vessel. In this case, the pointer 76a is used for designate a certain position on the display portion 75. In the following description, a blood vessel designated by the examiner will be referred to as a designated blood vessel.

The control portion 70 receives instructions from the examiner (Step 2-3). For example, the control portion 70 receives instructions from the examiner based on the signal output from the operation portion 76. For instance, the control portion 70 may obtain the position designated by the examiner (designated position) through the pointing device of the operation portion 76.

The control portion 70 obtains information about to which position in the observation image D2 the position designated on the motion contrast image corresponds (Step 2-4). For example, based on the association information on the observation image D2 and the motion contrast image D1 stored in the memory 72, the control portion 70 obtains the correspondence position on the observation image corresponding to the xy coordinates of the position designated on the motion contrast image. For instance, from the correspondence information stored in the memory 72, the control portion 70 obtains the xy coordinates on the observation image corresponding to the xy coordinates of the designated blood vessel.

When the correspondence position of the designated blood vessel on the observation image is obtained, the control portion 70 sets the correspondence position as a tracking position (Step 2-5) and starts scanning (Step 2-6). While performing tracking such that the correspondence position can be scanned at all times, the control portion 70 performs scanning plural times at time intervals. For example, the control portion 70 may perform scanning by using the measurement light and simultaneously capture the observation image continually, thereby correcting the scanning position according to the positional deviation of the fundus shown in the updated observation image.

More specifically, the control portion 70 compares a still image of the observation image D2, which is used for being associated with the motion contrast image D1, with the current observation image D2, and detects (calculates) the direction and amount of the positional deviation by image processing. For example, the control portion 70 uses, as a standard image, the still image data of the observation image D2 associated with the motion contrast image D1, and calculates the direction and amount of the positional deviation between the standard image and the observation image obtained in real time. In this way, positional deviation information on the still image is obtained.

When the direction and amount of the positional deviation are detected as described above, the control portion 70 appropriately controls the driving of the two galvano mirrors of the optical scanner 108 so as to correct the deviation of the scanning position. In this way, the scanning position is corrected. Even when the positional deviation of the subject's eye occurs, the scanning position can be corrected in the aforementioned manner, and the control portion 70 can obtain a plurality OCT signals, which is temporally different from each other with respect to the same scanning position, at all time.

By using the plurality of OCT signals obtained in Step 2-6 and the three-dimensional structure of the blood vessel obtained from the three-dimensional motion contrast image, the control portion 70 calculates an absolute blood flow velocity (Step 2-7). For example, the control portion 70 determines the Doppler phase shift from the plurality of OCT signals. The control portion 70 may calculate the absolute blood flow velocity, from the determined phase difference and the blood flow direction obtained from the three-dimensional structure of the blood vessel.

Figure 9:
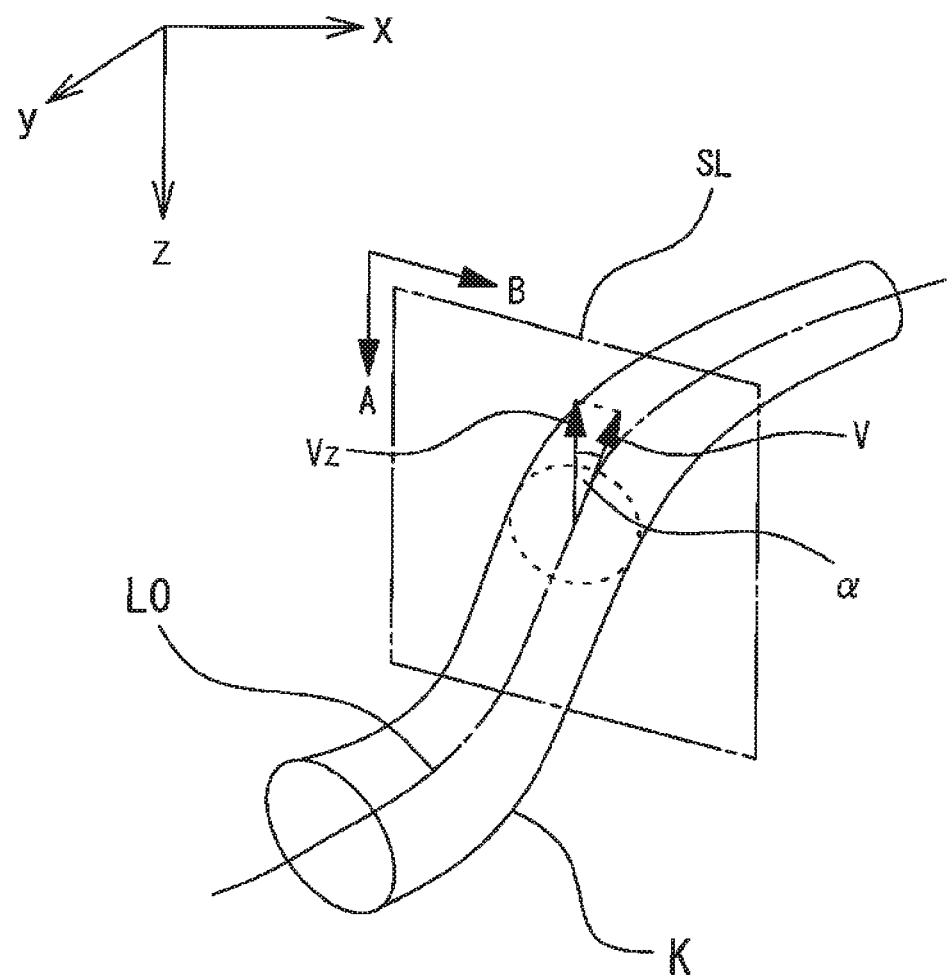
FIG. 9 is a view illustrating a method for determining a blood flow velocity.
Figure 10:
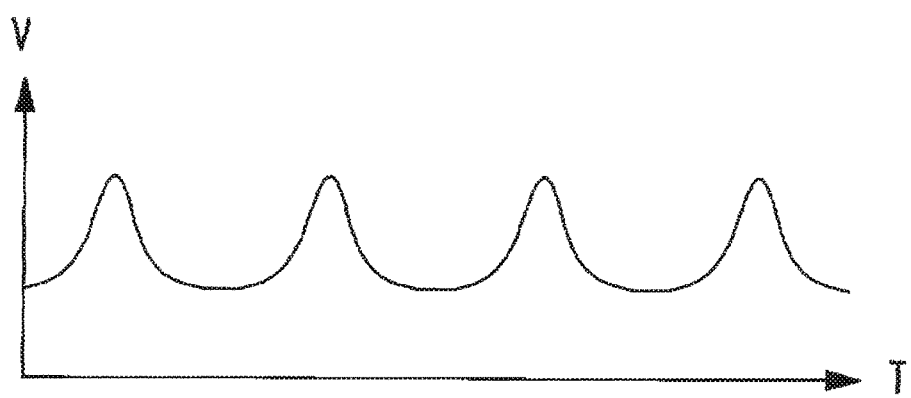
FIG. 10 is a view showing the relationship between time and the blood flow velocity.

As the method for determining the blood flow direction from the three-dimensional structure of the blood vessel obtained from the motion contrast image D1, a method of performing thinning on the three-dimensional structure of the blood vessel is exemplified. For example, as shown in FIG. 9, through the thinning processing, a three-dimensional vascular structure K can be expressed as a single line L0. For instance, the control portion 70 may regard the slope of the line L0 with respect to the measurement light scanning a scan line SL as the blood flow direction, and calculate the absolute blood flow velocity from the phase difference described above.

<Calculation of Blood Flow Velocity>

The absolute blood flow velocity will be described. A component vz of an absolute blood flow velocity v in the optical axis direction is represented by the following Equation (2) by using an angle α between the measurement light and a blood vessel.

$$v = \frac{v_z}{\cos\alpha} \tag{2}$$

Herein, the component vz is represented by the following Equation (3) by using a phase difference ΔΦ Doppler (−π to π), a refractive index n of vascular tissue, a central wavelength k, and a time interval T.

$$v_z = \frac{\Delta\Phi_{Doppler}}{2nkT} \quad (3)$$

By using two equations described above, the absolute blood flow velocity v is determined from the phase difference through the following Equation (4).

$$v = \frac{\Delta\Phi_{Doppler}}{2nkT\cos\alpha} \quad (4)$$

As described above, in the present example, the control portion 70 measures the blood flow of the subject's eye by using the three-dimensional motion contrast image D1 and a plurality OCT signals which is different from each other for the same scanning position. The control portion 70 can obtain the blood flow direction from the three-dimensional structure of the blood vessel obtained by the three-dimensional motion contrast image D1. Therefore, the control portion 70 can measure the absolute blood flow velocity of the subject's eye from the Doppler shift. As a result, for example, by comparing blood flow velocities of a plurality of test subjects, the control portion 70 can obtain information useful for diagnosing the subject's eye.

In the present example, the control portion 70 uses the blood flow direction, which is obtained from the three-dimensional motion contrast image D1 acquired in advance, for calculating the absolute blood flow velocity. Accordingly, if a plurality of OCT signals, which is temporally different from each other with respect to the same position in the subject's eye, is continuously obtained by using the OCT optical system, the control portion 70 can obtain the absolute velocity of the dynamic blood flow considering the influence of heartbeat of the test subject (see FIG. 10). In this way, by obtaining the temporal change of the blood flow velocity, the control portion 70 can provide the information which can be used for detecting diseases such as arteriosclerosis.

In the present example, the control portion 70 associates the position of the blood vessel checked in the motion contrast image D1 with the observation image D2, and performs tracking based on the association information. For example, because it takes a time to generate the motion contrast image D1, it is difficult to obtain the deviation information for following the minute motion of the subject's eye. In contrast, compared to the motion contrast image, the observation image D2 is obtained within a short time. Therefore, the observation image is suitable for obtaining the deviation information for following the minute motion of the subject's eye. As the control portion 70 of the present example, by associating the position of a small blood vessel that is not easily checked in the observation image D2 with the position of the blood vessel in the motion contrast image, it is possible to perform tracking even though the blood vessel is a small blood vessel that is not easily checked in the observation image D2. In this way, the control portion 70 can easily and continuously obtain a plurality of OCT signals, which is temporally different from each other with respect to the same position, and can appropriately determine the absolute velocity of the dynamic blood flow of the test subject.

The control portion 70 may automatically set the scan width at the time of scanning the blood vessel designated by the examiner, according to the blood vessel diameter obtained from the motion contrast image. It goes without saying that the examiner may manually set the scan width.

The control portion 70 may set the time interval T at the time of scanning the blood vessel designated by the examiner, according to the blood vessel diameter obtained from the motion contrast image. It goes without saying that the examiner may manually set the time interval T.

The scanning direction at the time of scanning the blood vessel designated by the examiner may be perpendicular to the blood flow direction. For example, in an en-face direction (direction perpendicular to the measurement light), the control portion 70 may calculate a direction perpendicular to the blood flow direction of the designated blood vessel and perform scanning in the calculated direction. As described above, the blood flow direction of the blood vessel may be determined by performing thinning on the three-dimensional structure of the blood vessel. For the thinning, for instance, known algorithms such as morphology processing, distance transform processing, Hilditch's algorithms, and Deutsch's algorithm may be used.

In this way, by performing scanning in a direction perpendicular to the blood flow direction, the control portion 70 does not need to consider the scan angle with respect to the blood flow direction at the time of calculating the blood flow velocity, and thus the calculation processing can be simplified. For example, the control portion 70 may automatically set the radial direction of the designated blood vessel as the scanning direction. It goes without saying that the control portion 70 may set the scan line based on the operation signal output from the operation portion 76 in response to the operation of the examiner.

Whenever the examiner newly designates a blood vessel in the motion contrast image shown in FIG. 8, the control portion 70 may determine the blood flow velocity by performing scanning while tracking the blood vessel designated as described above.

<Method for Detecting Positional Deviation>

As the method for detecting the positional deviation between two observation images at the time of tracking, it is possible to use various image processing methods (a method of using various correlation functions, a method of using Fourier transform, and a method based on matching of characteristic points).

For example, it is possible to consider a method of causing positional deviation in a predetermined standard image (such as the past en-face image) or a target image (current en-face image) by one pixel, comparing the standard image and the target image with each other, and detecting the positional deviation between the two data that occurs at the time when the two data agree with each other the most (at the time when the correlation becomes the highest). Furthermore, it is possible to consider a method of extracting characteristics points common to a predetermined standard image and a target image and detecting the positional deviation of the extracted characteristics points.

As a function for determining the positional deviation between two images, a phase-only-correlation function may be used. In this case, first, by Fourier transform performed on the respective images, the phase and amplitude of the respective frequency components are obtained. Herein, the obtained amplitude component is normalized to a magnitude 1 for the respective frequency components. Thereafter, the phase difference between the two images is calculated for each frequency, and then the obtained results are subjected to inverse Fourier transform.

When there is no positional deviation between two images, only cosine waves are added up, and a peak appears in the position of origin (0,0). Furthermore, when there is positional deviation, a peak appears in a position corresponding to the positional deviation. Therefore, by determining the position where a peak is detected, the positional deviation between the two images is obtained. According to this method, it is possible to detect the positional deviation of an en-face image within a short time with high accuracy.

Figure 11A:
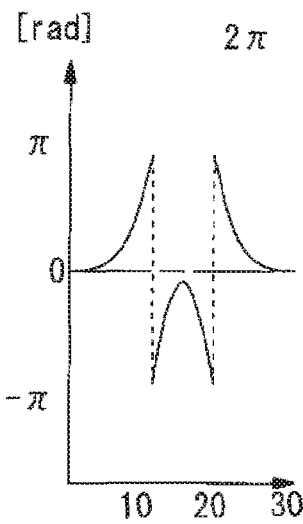
FIGS. 11A to 11F is a view for illustrating a profile of phase difference.

As described in Equation (2), the phase difference $\Delta\Phi$ Doppler falls into a range of $-\pi$ to $\pi$ by invert tangent calculation. Therefore, in a case where the time interval T between the scanning operations, if blood flows rapidly, the phase difference $\Delta\Phi$ Doppler is beyond the range of $-\pi$ to $\pi$. For example, as shown in FIG. 11A, the profile of the phase difference $\Delta\Phi$ Doppler in the scanning direction becomes discontinuous. In this case, it is difficult to diagnose the subject's eye while measuring velocity from the detected profile. Therefore, as in the present example, for example, the control portion 70 performs scanning by searching for an appropriate time interval T.

Hereinafter, a method will be described in which scanning is performed at an appropriate time interval T during the scan signal-obtaining processing in Step 2-6 such that the phase difference $\Delta\Phi$ Doppler is not beyond the range of $-\pi$ to $\pi$. In the following description, a case where the phase difference $\Delta\Phi$ Doppler is beyond the range of $-\pi$ to $\pi$ and thus discontinuous points are generated is expressed as "lapped".

Examples of the method of performing scanning at an appropriate interval includes a method in which the control portion 70 performs scanning while sequentially changing the time interval T for each scanning operation. In the following description, the control portion 70 performs scanning while sequentially shortening the long time interval T. In this case, by using the obtained plurality of OCT signals, the control portion 70 sequentially calculates the phase differences $\Delta\Phi$ Doppler obtained at different time intervals T, and determines whether or not the calculated phase differences $\Delta\Phi$ Doppler are lapped. Thereafter, for example, the control portion 70 continues scanning at a time interval T, which is fixed when it is determined that the phase differences $\Delta\Phi$ Doppler are not lapped, or at a time interval T which is shorter than the aforementioned time interval T.

Figure 11C:
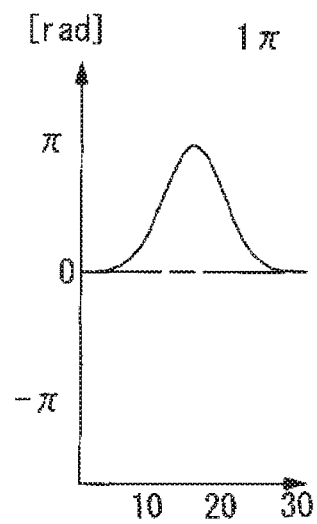
Figure 11E:
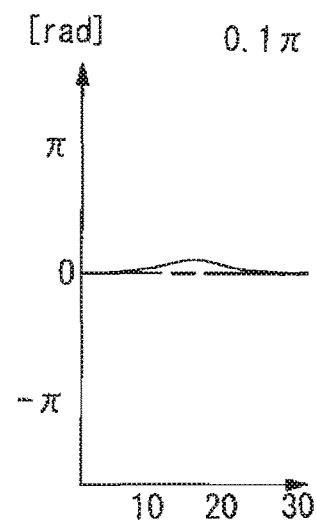
Figure 11B:
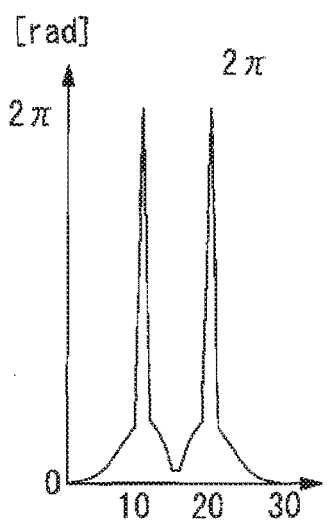
Figure 11D:
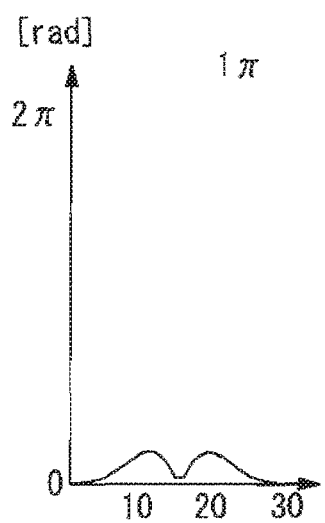

Examples of the method for determining whether or not the phase differences $\Delta\Phi$ Doppler are lapped include a method in which the determination is performed based on the degree of change of the phase difference $\Delta\Phi$ Doppler in pixels adjacent to each other. In this case, the control portion 70 may apply an edge detection filter (such as differential processing like a Laplacian filter) to the phase differences $\Delta\Phi$ Doppler obtained from a plurality of OCT signals. For example, as shown in FIG. 11A, when the edge detection filter is applied to the profile of the lapped phase differences $\Delta\Phi$ Doppler, the intensity in the position where the signals are lapped is locally increased as shown in FIG. 11B. In contrast, as shown in FIG. 11C, when the edge detection filter is applied to the profile of the non-lapped phase differences $\Delta\Phi$ Doppler, the local increase of the intensity does not occur as shown in FIG. 11D. Accordingly, for instance, the control portion 70 may determine that the phase differences $\Delta\Phi$ Doppler are not lapped when the average of the profiles after the application of the edge detection filter is equal to or less than a predetermined value. It goes without saying that the control portion 70 may determine that the phase differences $\Delta\Phi$ Doppler are not lapped when the maximum value after the application of the edge detection filter is equal to or less than a predetermined value.

As described above, by appropriately setting the time interval T, the control portion 70 can obtain non-lapped phase differences $\Delta\Phi$ Doppler, regardless of the difference in the blood flow velocity. By obtaining the non-lapped phase differences $\Delta\Phi$ Doppler, the laminar flow state of the blood flow can be excellently ascertained and used for diagnosis or the like for the subject's eye. Furthermore, the examiner can save effort to set the time interval T on his/her own.

The control portion 70 may search for the time interval T which increases the signal intensity of the phase difference $\Delta\Phi$ Doppler as much as possible. For example, when it is determined that the phase differences $\Delta\Phi$ Doppler are not lapped, the control portion 70 may gradually lengthen the time interval T such that the maximum value of the profile of the phase differences $\Delta\Phi$ Doppler within the range of $-\pi$ to $\pi$ is increased as much as possible, and search for an appropriate time interval T.

In the above description, the control portion 70 sequentially shortens a long time interval T. When the time interval T is long, the phase differences $\Delta\Phi$ Doppler as the Doppler signals resulting from the blood flow increase and are highly likely to be lapped. When the time interval T is intentionally gradually shortened from the lapped state as described above so as to obtain non-lapped phase differences $\Delta\Phi$ Doppler, it is highly likely that high-intensity signals can be obtained within a range of $-\pi$ to $\pi$.

Figure 11F:
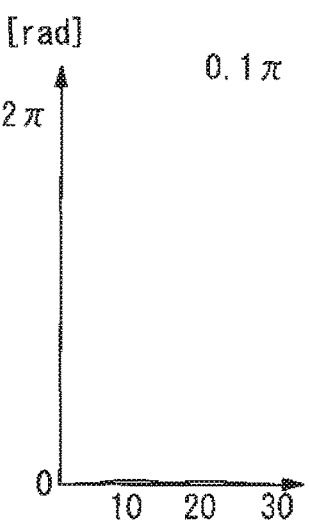

It goes without saying that the control portion 70 may lengthen a short time interval T. If the time interval T is short, the phase differences $\Delta\Phi$ Doppler as the Doppler signals resulting from the blood flow are reduced, and non-lapped phase differences $\Delta\Phi$ Doppler can be rapidly obtained. However, if the time interval T is short, the signal intensity is reduced as shown in FIGS. 11E and 11F, and the signals are likely to be buried under a noise floor. Therefore, the control portion 70 may search for a long time interval T as much as possible within a range in which the signals are not lapped.

In the example described above, the time interval T is gradually lengthened or shortened, but the present invention is not limited thereto. For example, the control portion 70 may alternately lengthen and shorten the time interval T or randomly change the time interval T. Whether the time interval T is to be shortened or lengthened may be set according to the operation signal output from the operation portion by the operation of the examiner.

The control portion 70 may determine the absolute blood flow velocity at a certain point in time by using a plurality of OCT signals obtained for generating the three-dimensional motion contrast image D1, and set the initial time interval T based on the magnitude of the velocity. Thereafter, the control portion 70 may determine an appropriate time interval T by sequentially changing the time interval T as described above. In this way, by setting the time interval T based on the absolute blood flow velocity at a point in time when the three-dimensional motion contrast image D1 is obtained, it is possible to shorten the time taken for setting an appropriate time interval T.

The magnitude of the blood flow velocity can be estimated to some extent from the thickness, type (such as an artery or a vein), and the like of the blood vessel. Accordingly, the control portion 70 may set the time interval T based on the blood flow velocity estimated from the thickness, type, and the like of the designated blood vessel. In this case, for instance, the control portion 70 obtains the correspondence relationship between the thickness, type, and the like of the blood vessel and the magnitude of the blood flow velocity from the past measurement data, and stores the correspondence relationship in the memory 72 in the form of a correspondence table. Furthermore, the control portion 70 may estimate the blood flow velocity of the designated blood vessel by checking at least either the estimated size of the blood vessel or the type of the blood vessel estimated from the depth of retina where the blood vessel exists against the correspondence table stored in the memory 72.

For example, the control portion 70 may obtain a plurality of OCT signals at a plurality of different time intervals T, and among ΔΦ Doppler calculated from the obtained plurality of OCT signals, those not being lapped may be used for calculating the blood flow velocity.

In the above description, for example, the control portion 70 changes the time interval T, but the present invention is not limited thereto. For instance, the control portion 70 may perform scanning at a certain time interval T and calculate the absolute blood flow velocity by selecting a combination of OCT signals, in which the calculated phase differences ΔΦ Doppler are not lapped, from the obtained plurality of OCT signals. For example, the control portion 70 may perform scanning at a short time interval T and calculate ΔΦ Doppler by thinning out data from the obtained plurality of OCT signals. For instance, in a case where the control portion 70 performs scanning at 0.5 msec of a time interval T, the control portion 70 may thin out data from the obtained plurality of OCT signals and calculate ΔΦ Doppler from the OCT signals obtained at a time interval T (such as 1.0 msec, 1.5 msec, or 2.0 msec) which is a multiple of 0.5. In this case, for example, for calculating the blood flow velocity, the control portion 70 may use OCT signals in which ΔΦ Doppler are not lapped or OCT signals in which a maximum value of ΔΦ Doppler is great, among the OCT signals obtained at each time interval T. Furthermore, among OCT signals obtained at each time interval T, those in which the minimum value of the slope (such as a differential value) of ΔΦ Doppler is small may be used for calculating the blood flow velocity.

In this way, an appropriate time interval T may be searched for simply by changing the calculative time interval T without changing the time interval T at which the measurement light is actually radiated.

What is claimed is:

1. An optical coherence tomography device comprising:
    an OCT optical system including a scanner configured to scan a test subject by measurement light, the OCT optical system being configured to detect an OCT signal generated based on the measurement light and reference light corresponding to the measurement light;
    a processor; and
    memory storing instructions, when executed by the processor, causing the optical coherence tomography device to execute:
    an image generation processing of processing a plurality of first OCT signals, which are temporally different from each other with respect to a same position on the test subject, and generating, based on the plurality of first OCT signals, a three-dimensional motion contrast image, which is obtained by imaging distribution of a moving object in a depth direction in each of the scanning position;
    a Doppler shift detection processing of processing a plurality of second OCT signals which are temporally different from each other with respect to the same position on the test subject, and detecting Doppler shift in a depth direction in a scanning position specified on the three-dimensional motion contrast image, the plurality of second OCT signals being detected at timings different from the timings when the plurality of first OCT signals are detected; and
    a velocity obtaining processing of obtaining an absolute velocity of the moving object based on the Doppler shift detected by the Doppler shift detection processing and a three-dimensional structure of the test subject obtained from the three-dimensional motion contrast image generated by the image generation processing.

2. The optical coherence tomography device according to claim 1 further comprising an observation optical system configured to obtain an observation image of the test subject,
    wherein the instructions when executed by the processor causes the optical coherence tomography device to execute:
    an association processing of associating the scanning position specified on the three-dimensional motion contrast image with the observation image obtained by the observation optical system;
    a deviation detection processing of detecting positional deviation between the observation image associated with the scanning position and a current observation image obtained by the observation optical system by image processing; and
    a scanning position correction processing of controlling driving of the scanner based on a detection result of the positional deviation detected by the deviation detection processing and correcting the scanning position of the measurement light used at the time of detecting the Doppler shift.

3. The optical coherence tomography device according to claim 1, further comprising:
    a signal receiver configured to receive an operation signal output from an operation unit by an operation of an examiner;
    wherein the instructions when executed by the processor causes the optical coherence tomography device to execute:
    a first scanning position setting processing of setting, as a scanning position of the measurement light used at the time of detecting the Doppler shift, a position which is specified on the three-dimensional motion contrast image based on the operation signal received by the signal receiver.

4. The optical coherence tomography device according to claim 1, wherein the velocity obtainment processing obtains a three-dimensional structure of a blood vessel of the test subject based on the three-dimensional motion contrast image generated by the image generation processing, and obtains an absolute blood flow velocity, based on the Doppler shift detected by the Doppler shift detection processing and the three-dimensional structure of the blood vessel of the test subject.

5. The optical coherence tomography device according to claim 1, wherein
    the instructions when executed by the processor causes the optical coherence tomography device to execute:
    a second scanning position setting processing of obtaining a movement direction of the moving object based on the three-dimensional structure of the test subject and setting a scanning position in a direction orthogonal to the obtained movement direction.

6. The optical coherence tomography device according to claim 3, wherein
the three-dimensional structure of the test subject is a three-dimensional structure of a blood vessel, and
the first scanning position setting processing obtains a size of a diameter of the blood vessel based on the three-dimensional structure of the blood vessel and sets a scan width of the measurement light to be greater than the obtained size of the blood vessel diameter.

7. The optical coherence tomography device according to claim 1, wherein
the instructions when executed by the processor causes the optical coherence tomography device to execute:
a blood vessel structure obtaining processing of obtaining a three-dimensional structure of a blood vessel of the test subject based on the three-dimensional motion contrast image generated by the image generation processing, and
a time interval control processing of obtaining a diameter of the blood vessel based on the three-dimensional structure of the blood vessel and changing a time interval of irradiation with respect to the same position according to the obtained size of the blood vessel diameter.

8. The optical coherence tomography device according to claim 2, wherein the observation optical system includes an infrared imaging optical system configured to image the test subject by using infrared light.

9. The optical coherence tomography device according to claim 2, wherein the observation optical system includes a scanning laser ophthalmic optical system configured to image the test subject by using a confocal optical system.

10. The optical coherence tomography device according to claim 1, wherein
the instructions when executed by the processor causes the optical coherence tomography device to execute:
a first control processing of obtaining the plurality of first OCT signals for each of a plurality of scan lines by controlling the scanner in such a manner that each of the plurality of scan lines is scanned plural times with the measurement light.

11. The optical coherence tomography device according to claim 1, wherein
the instructions when executed by the processor causes the optical coherence tomography device to execute:
a second control processing of obtaining the plurality of second OCT signals by controlling the scanner in such a manner that a scan line corresponding to the scanning position specified on the three-dimensional motion contrast image is scanned plural times with the measurement light.

12. A non-transitory computer readable medium storing a control program used in an optical coherence tomography device including an OCT optical system including a scanner configured to scan a test subject by measurement light, the OCT optical system being configured to detect an OCT signal generated based on the measurement light and reference light corresponding to the measurement light, the control program, when executed by a processor of the optical coherence tomography device, causing the optical coherence tomography device to execute:
an image generation processing of processing a plurality of first OCT signals, which are temporally different from each other with respect to a same position on the test subject, and generating, based on the plurality of first OCT signals, a three-dimensional motion contrast image, which is obtained by imaging distribution of a moving object in a depth direction in each of the scanning position;
a Doppler shift detection processing of processing a plurality of second OCT signals which are temporally different from each other with respect to the same position on the test subject, and detecting Doppler shift in a depth direction in a scanning position specified on the three-dimensional motion contrast image, the plurality of second OCT signals being detected at timings different from the timings when the plurality of first OCT signals are detected; and
a velocity obtaining processing of obtaining an absolute velocity of the moving object based on the Doppler shift detected by the Doppler shift detection processing and a three-dimensional structure of the test subject obtained from the three-dimensional motion contrast image generated by the image generation processing.

13. An optical coherence tomography device comprising:
an OCT optical system including a scanner configured to scan a test subject by measurement light, the OCT optical system being configured to detect an OCT signal generated based on the measurement light and reference light corresponding to the measurement light;
a processor; and
memory storing instructions, when executed by the processor, causing the optical coherence tomography device to execute:
a motion contrast obtaining processing of obtaining motion contrast of a plurality of OCT signals obtained at a first time interval with respect to the same position on the test subject and obtaining a profile of a phase difference between the plurality of OCT signals,
wherein when the profile of the phase difference is discontinuous, the motion contrast obtaining process obtains the motion contrast of the plurality of OCT signals at a second time interval different from the first interval.

14. The optical coherence tomography device according to claim 13, wherein
the instructions when executed by the processor causes the optical coherence tomography device to execute a determination processing of detecting a slope of the profile of the phase difference obtained by the motion contrast obtaining process and determining whether or not the profile of the phase difference is continuous based on the detected slope.

15. The optical coherence tomography device according to claim 13, wherein the second time interval is shorter than the first time interval.

16. The optical coherence tomography device according to claim 13, wherein
the instructions when executed by the processor causes the optical coherence tomography device to execute a driving control processing of changing a time interval of irradiation of the measurement light with respect to the same position by controlling the driving of the scanner when the profile of the phase difference is discontinuous.

17. The optical coherence tomography device according to claim 13, wherein the motion contrast obtaining processing selects at least one group of OCT signals, which are obtained at the second time interval, from the plurality of OCT signals obtained at the first time interval when the obtained profile of the phase difference is discontinuous and obtains the motion contrast of the selected group of OCT signals.

18. The optical coherence tomography device according to claim 13, wherein when the profile of the phase difference is continuous, the motion contrast obtaining processing obtains the motion contrast of the plurality of OCT signals obtained at a third time interval longer than the first time interval so as to increase a signal-to-noise ratio of the motion contrast.

19. An optical coherence tomography device comprising:
an OCT optical system including a scanner configured to scan a test subject by measurement light, the OCT optical system being configured to detect an OCT signal generated based on the measurement light and reference light corresponding to the measurement light;
a processor; and
memory storing instructions, when executed by the processor, causing the optical coherence tomography device to execute:
a motion contrast obtaining processing of obtaining motion contrast of a plurality of OCT signals which is obtained at a first time interval with respect to a same position on the test subject, and obtaining a profile of a phase difference between the plurality of OCT signals;
a three-dimensional structure obtaining processing of obtaining a three-dimensional structure of a blood vessel of the test subject based on the motion contrast; and
a blood vessel information obtaining processing of obtaining at least either a diameter or a type of a blood vessel based on the three-dimensional structure of the blood vessel, wherein when the profile of the phase difference between the plurality of OCT signals is discontinuous, the motion contrast obtaining processing obtains the motion contrast of the plurality of OCT signals obtained at a second time interval different from the first time interval based on the diameter or the type of the blood vessel obtained by the blood vessel information obtaining processing, the second time interval being preset according to the obtained diameter or the type of the blood vessel.

20. A non-transitory computer readable medium storing a control program used in an optical coherence tomography device including an OCT optical system including a scanner configured to scan a test subject by measurement light, the OCT optical system being configured to detect an OCT signal generated based on the measurement light and reference light corresponding to the measurement light, the control program, when executed by a processor of the optical coherence tomography device, causing the optical coherence tomography device to execute:
obtaining a phase difference of a plurality of OCT signals, which is obtained at a first time interval with respect to a same position on the test subject; and
obtaining a phase difference of a plurality of OCT signals which is obtained at a second time interval different from the first time interval when a profile of the obtained phase difference is discontinuous.

* * * * *